United States Patent
Lakies

(10) Patent No.: US 10,960,240 B2
(45) Date of Patent: Mar. 30, 2021

(54) DEVICE FOR THE PROVISION OF OXYGEN MASKS WHEN REQUIRED

(71) Applicant: Airbus Operations GmbH, Hamburg (DE)

(72) Inventor: Marcel Lakies, Hamburg (DE)

(73) Assignee: Airbus Operations GmbH

(*) Notice: Subject to any disclaimer, the term of this patent is extended or adjusted under 35 U.S.C. 154(b) by 279 days.

(21) Appl. No.: 16/210,350

(22) Filed: Dec. 5, 2018

(65) Prior Publication Data
US 2019/0209876 A1 Jul. 11, 2019

(30) Foreign Application Priority Data

Jan. 5, 2018 (DE) ..................... 10 2018 100 170.3

(51) Int. Cl.
*A62B 25/00* (2006.01)
*A62B 7/14* (2006.01)

(52) U.S. Cl.
CPC ............... *A62B 25/00* (2013.01); *A62B 7/14* (2013.01); *A62B 25/005* (2013.01); *A61M 2202/0208* (2013.01); *B64D 2231/025* (2013.01)

(58) Field of Classification Search
CPC .. A61M 16/06; A61M 2202/028; B64D 11/00
See application file for complete search history.

(56) References Cited

U.S. PATENT DOCUMENTS

| 4,154,237 | A | 5/1979 | Courter | |
|---|---|---|---|---|
| 6,497,386 | B2* | 12/2002 | Martinez | B64D 10/00 128/206.27 |
| 7,431,034 | B2 | 10/2008 | Westphal et al. | |
| 7,585,022 | B2 | 9/2009 | Achilles et al. | |
| 7,621,275 | B2 | 11/2009 | Fischer | |
| 8,745,965 | B2 | 6/2014 | Tiegs et al. | |
| 2015/0035424 | A1* | 2/2015 | Rittner | B64D 11/003 312/327 |

FOREIGN PATENT DOCUMENTS

| DE | 10 2004 009 346 A1 | 9/2005 |
|---|---|---|
| DE | 10 2004 017 078 A1 | 11/2005 |
| DE | 10 2004 026 649 A1 | 1/2006 |
| DE | 10 2011 102 115 A1 | 11/2012 |
| EP | 0 191 610 B1 | 1/1988 |
| EP | 1 654 158 B1 | 7/2007 |

* cited by examiner

*Primary Examiner* — Rachel T Sippel
(74) *Attorney, Agent, or Firm* — Lerner, David, Littenberg, Krumholz & Mentlik, LLP

(57) ABSTRACT

A device for provision of oxygen masks has a container, which can be closed by a cover, for accommodating one or more oxygen masks, at least one extendable arm having an outer end, and a driving device. The outer end is coupled to at least one oxygen mask. The arm is designed to adopt a storage position, wherein the arm is arranged completely within the container, and an extended position, wherein the outer end is extended out of the container and the arm holds the at least one oxygen mask coupled thereto laterally at a distance from the container. For extension, the driving device is coupled to the arm. The arm has an end piece, on which a wound-up hose can be releasably fixed. A fixing device is formed on the end piece in such a way as to release the wound-up hose when the extended position is reached.

12 Claims, 2 Drawing Sheets

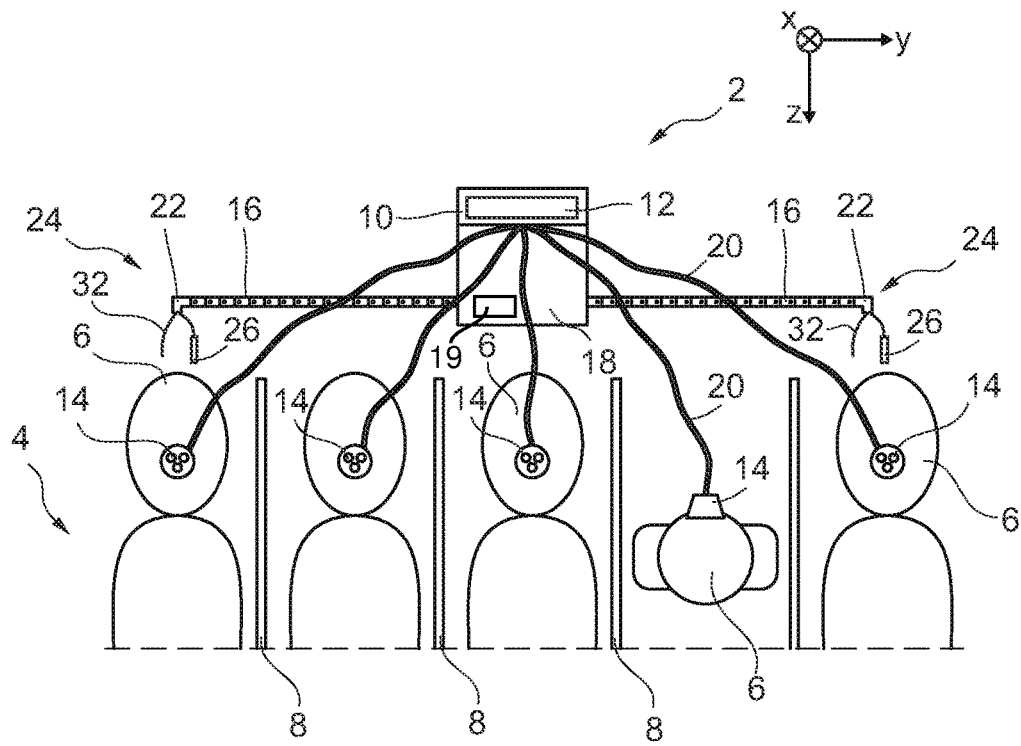
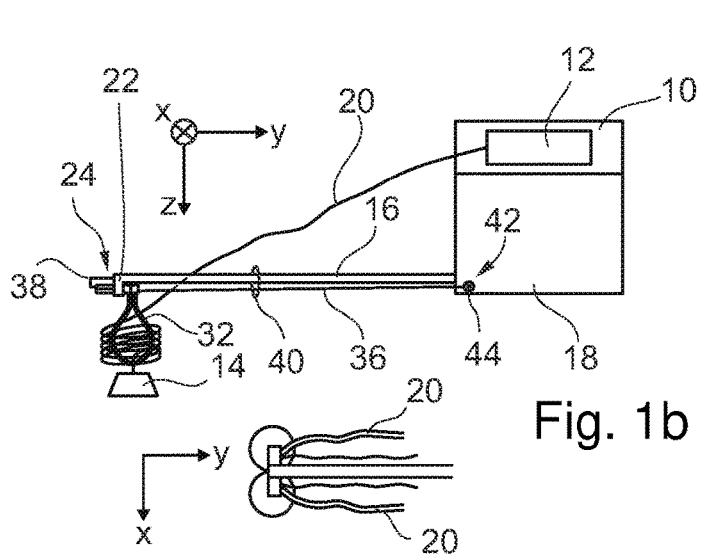
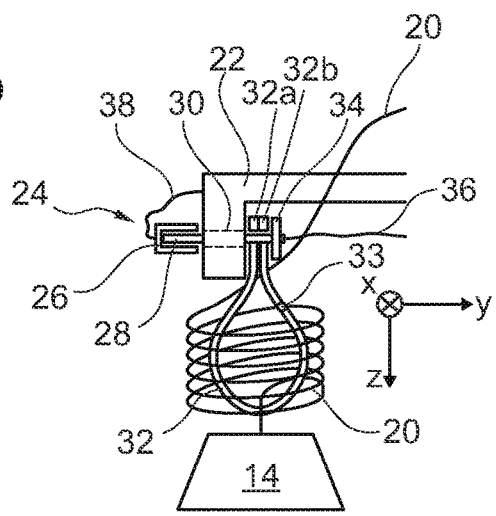
Fig. 1a
Fig. 1b
Fig. 1d
Fig. 1c

DEVICE FOR THE PROVISION OF OXYGEN MASKS WHEN REQUIRED

FIELD OF THE INVENTION

The invention relates to a device for the provision of oxygen masks when required, to a method for the provision of oxygen masks when required in an aircraft, and to a vehicle having a device for the provision of oxygen masks when required.

BACKGROUND OF THE INVENTION

Oxygen masks are carried in aircraft and, especially, passenger aircraft which fly at high altitudes and have a pressurized cabin. They are dropped automatically from a container above a seat in the event of a pressure drop within the cabin. A person sitting below can grab the oxygen mask, pull it towards them and put it on. Certification regulations require that at least one oxygen mask must be positioned and presented visibly and in a way which enables it to be reached by each passenger (either seated or lying down) when strapped in. When pulled, the oxygen flow into the relevant oxygen mask is generally initiated by a corresponding mechanism. There are also other mechanisms for activating the oxygen flow.

In the case of passenger aircraft, there is a known practice of arranging the said containers for oxygen masks in a grid pattern in supply ducts or recesses situated above passenger seats in a ceiling panel, wherein the grid pattern corresponds substantially to the grid pattern of the passenger seats. In passenger cabins in which means for changing the layout when required are provided, passenger seats can occupy different positions within certain limits. As a result, it may be necessary to adjust the position of the containers in the overhead supply ducts accordingly.

With certain cabin configurations, individual seats may be at a large horizontal distance from the associated/nearest container. Cabin configurations of this kind can only be implemented, especially in terms of certification, if some or all of the stowed oxygen masks in affected containers are at a horizontal distance from the container after the container cover has been opened. Moreover, there can also be partitions or other obstacles between two adjacent seats. If these had the effect that not all the passengers could reach an oxygen mask in a strapped-in position, such a cabin configuration would not be eligible for approval. Moreover, there can be partitions or other obstacles between an oxygen container and the seats to be supplied by said container.

Devices for the provision of oxygen masks in which a certain variability of position can be compensated for are furthermore known. For example, EP 1 654 158 B1 discloses arranging an inflatable lever in a container of this kind, the lever being coupled to an oxygen mask. When the container is opened, the lever is automatically inflated and moves the oxygen mask away from the container in a horizontal direction.

BRIEF SUMMARY OF THE INVENTION

An aspect of the invention proposes an alternative device for providing oxygen masks when required, in which a greater horizontal spacing from the container is possible and, in particular, partitions or other obstacles can be overcome.

A device for the provision of oxygen masks when required is proposed. The device has a container, which can be closed by a cover, for accommodating one or more oxygen masks, at least one extendable arm having an outer end, and at least one driving device. The outer end is coupled to at least one oxygen mask. The arm is designed to adopt a storage position, in which the arm is arranged completely within the container, and at least one extended position, in which the outer end is extended out of the container and in which the arm holds the at least one oxygen mask coupled thereto at a lateral distance from the container. For extension, the driving device is coupled to the arm. The arm has an end piece, on which a wound-up hose can be releasably fixed. At least one fixing device is formed on the end piece in such a way as to release the wound-up hose when the extended position is reached.

The device according to an embodiment of the invention makes it possible to move oxygen masks from a container over obstacles and to let them drop only after an envisaged position has been reached. These obstacles can be, for instance, partitions between seats, which are particularly relevant for premium categories. The device according to an embodiment of the invention makes it possible to supplement conventional (or currently customary) cabin configurations with additional partitions or similar obstacles without the need for this purpose for additional containers to hold oxygen masks. The fewer containers have to be installed in the cabin, the less space the oxygen system takes up in the cabin. This space can be used for other systems. One prerequisite for this is that all the components involved in the sequence of motion are in the container before the opening of the container cover. Known concepts for moving oxygen masks are restricted to allowing the oxygen masks to drop in order subsequently to move them laterally. In the presence of partitions or other obstacles, these would not reach their envisaged target position.

In general, a certain horizontal distance between the container and a relevant seat can be bridged by this device. The arm can be implemented in various ways, e.g. as a single part or in several parts. Particularly in the case of the multi-part form, the length of the arm in the extended position can exceed any edge length of the container if a plurality of links is used. However, the type and embodiment of the arm and the driving device are not relevant to the attainment of the advantages mentioned.

At least one extended position in which an oxygen mask is released can be defined. This does not necessarily have to correlate with an end position of the arm. In particular, it is also possible to define additional extended positions, as explained below.

By way of example, it may be mentioned that a plurality of links coupled in an articulated manner can be guided out of the container. The links can enclose with respect to one another a pivoting range which extends as far as a level juxtaposition of the links. The arm can be designed in such a way, for instance, that, in an extended position, the arm adopts a level juxtaposition of the links under the action of gravity for the lateral spacing of the relevant oxygen mask from the container. The use of such articulatedly coupled links allows the selective provision of a level and preferably rectilinear arm without having to provide a correspondingly long stowage space of an arm. For this purpose, the joints could be designed such that a pivoting axis provided by the joints extends vertically, i.e. perpendicularly to the plane of extent of the level juxtaposition of the links. As an alternative, a pivoting axis of this kind can also extend horizontally, i.e. in the plane of extent of the level juxtaposition of the links and preferably perpendicularly to the extension movement. At the same time, a pivoting limit should be provided to ensure that the shape adopted by the links is maintained even under the action of gravity and subject to tensile forces exerted by the relevant oxygen mask.

Moreover, it is also possible to give consideration to a multi-part arm consisting of a plurality of links, each coupled so as to be pivotable about a vertical axis. These can be moved into an extended position by rotation about the respective vertical axis.

Integrating the end piece with the fixing device entails no change or no significant change to the container and the cover for closing the container. There is no particular need to modify the container or the cover as long as the end piece together with the fixing device fits into the container.

The type and embodiment of the driving device can depend on the design of the arm. It is possible, for example, for the driving device to have an electric motor and a transmission which is connected to the electric motor and is matched to the respective design of the arm. The transmission can be of self-locking design in order to hold a position of the arm, once reached. However, this is not necessary, and it is also possible to use a design that is not self-locking with other means for protecting the transmission.

However, other driving devices, which are based on stored mechanical energy, may also be considered for reasons of weight. Springs and other mechanisms, by means of which a certain mechanical energy can be stored and released, may be mentioned by way of example.

The driving device and the arm can be arranged on an inner side of the cover. A unit for holding or supporting the arm in the storage position can therefore likewise be arranged on the inner side of the cover.

As an alternative, the driving device and the arm can also be arranged directly in the container, independently of the cover.

The cover can be embodied in such a way that, under the action of gravity, it rotates about an axis at one edge, e.g. from a horizontal position to a vertical position. When the driving device and the arm are accommodated, the mass of the cover may increase as compared with known containers. To prevent the risk of injury in the event of contact with the head, a damper may be used to damp the rotary motion of the cover.

The end piece of the arm should be regarded as a component which is furthest away from the container in the extended position of the arm. The end piece is provided for the purpose of releasably fixing a wound-up hose. This means that the oxygen mask with the wound-up hose is guided out of the container in an essentially two-stage movement. After the opening of the container, a lateral movement is first of all carried out by the extendable arm. By means of this, the end piece with the wound-up hose is moved out of the container to the extended position. The fixing device then releases the hose in the extended position. As a result, the relevant oxygen mask can drop from the arm, enabling a passenger to grab the mask at the relevant position.

At this point, it may be observed that the two-stage embodiment does not strictly have to have two mutually independent movement steps. On the contrary, it is also conceivable for the fixing device to release the wound-up hose precisely when the arm is in the process of reaching the extended position. Consequently, it may be that the end piece will move slightly further with the fixing device open.

Overall, the device according to an embodiment of the invention makes it possible to achieve an individually adaptable distance between an oxygen mask and a container which can even overcome obstacles, e.g. partitions.

In an advantageous embodiment, the at least one fixing device has a loop that can be closed by a securing element in order to fix the hose, wherein the securing element is connected to the container by a holding element which is flexible and resistant to tension. Here, the holding element has a free length outside the container which is less than or corresponds to the free length of the extended arm outside the container, with the result that, on reaching the length of the relevant holding element, the securing element is pulled out of the fixing device when the arm reaches the relevant extended position. The flexible holding element can be in the form of a cord, a tape, a chain or a similar element. This is provided for the purpose of providing a mechanical limitation of the movement of the securing element when the end piece is moved into the extended position. The securing element is then consequently subjected to a tensile force. The tensile force pulls it out of a position in which it secures the loop. When the securing pin is removed, the loop opens and releases the wound-up hose, causing the associated oxygen mask to drop down. The special advantage of this embodiment consists in the entirely passive, mechanical design. The securing element does not have to be released by active drive means or the like to bring about opening of the loop in the envisaged position. It is thus furthermore ensured that the loop does not open before the target position has been reached. This prevents a mask from dropping down in front of an obstacle instead of behind it, thereby making the mask inaccessible to the passenger concerned (in the strapped-in position).

One special advantage can furthermore be achieved by the fact that it is also possible for a plurality of oxygen masks to be fixed on an arm by means of loops. These can each be fixed with a dedicated holding element on the end piece of the arm. The lengths of the holding elements are matched to the respective positions of the passenger seats assigned to the container under consideration. During the movement of the arm into the extended position, it is therefore also possible for two or more oxygen masks to be released at different positions.

The holding element can be held on a drum rotatably mounted in the container in such a way that the holding element can be unwound. Depending on the distance travelled by the end piece, it may be appropriate to give the holding element a defined accommodation space, from which it can be guided in a precise manner. It is thereby possible to protect other mechanical elements, that is to say, for instance, the arm, from being jammed or tangled up in the holding element. One particularly simple variant in this context is to accommodate the holding element on a drum. This can be rotatably mounted in a simple manner and can release the holding element when subjected to a tensile force. The rotatable mounting can be implemented in the form of a simple sliding fit. For this purpose, the drum has a hole, by means of which the drum is mounted on a pin or the like.

On the other hand, the holding element can be arranged in a guide channel of the container. The guide channel can be arranged within the cover or the container. Depending on the length of the arm in the extended position thereof, the guide channel can extend at least once around an inner side of the container or an edge of the cover.

It should be ensured that the holding element is locked precisely in an end position. This can be accomplished by welding, adhesive bonding or tying the holding element to the drum or to the guide channel. When using the guide channel, it is, however, also possible to mount a stop on one end of the holding element, this being larger than a through opening in the guide channel and consequently locks with said opening.

The at least one fixing device is preferably designed to fix the securing element positively or non-positively in a releasable manner. Accidental release of the securing element without the action of the holding element can thereby be prevented. In a simple case, the releasable retention can be implemented by slight jamming of the securing element in an opening or the like.

The at least one fixing device preferably has a sleeve having a sleeve bore, wherein the securing element has a securing pin, which is designed to correspond to the sleeve bore. The securing pin can have an alignment which corresponds to the direction of extension. As the arm is extended, the securing pin can therefore be released easily from the bush by the action of a tensile force.

The sleeve can be magnetic, at least in some region or regions, and can be designed to retain the securing pin magnetically in a releasable manner. This enables the securing pin to be retained in a releasable manner. The magnetic force of the sleeve can be adapted to the arm or the driving device. The magnetic force is intended to ensure that the securing pin is not released from the sleeve by normal vibrations but only by a tensile force.

The at least one fixing device or the securing element can have a spring-mounted body which engages in a correspondingly shaped recess in the respective other element of the fixing device or the securing element, for releasable retention. A body of this kind can, for instance, apply a force to the securing element which is directed transversely to the main direction of extent of said element. If the securing element has a recess into which the body can engage, a releasable positive joint can thereby be achieved. Given a suitable design of the shape of the body, of the recess and of the spring force, a tensile force acting on the securing element can move the body out of the recess, counter to the spring force acting on it, thereby releasing the securing element.

The device can have at least two extendable arms, which have different lengths in the extended position thereof. It is thereby possible to reach at least two passenger seats. It is thereby also possible, for example, to extend a relatively large number of oxygen masks.

The device can furthermore have at least two extendable arms, which can be extended in different directions. The device could, for instance, be arranged above a passenger seat which is adjacent on two sides to one or more passenger seats. There can be one or more partitions between individual seats and the container.

Furthermore, at least one arm, which has a plurality of fixing devices on the end piece, can be provided. A fixing device can release one or more masks at a defined position. For this purpose, the associated holding elements have different lengths.

The invention furthermore relates to a method for the selective provision of an oxygen mask in an aircraft, comprising steps of opening a cover of a container arranged in a recess in a ceiling region, extending an arm from a storage position into an extended position by means of a driving device, wherein at least one oxygen mask is coupled to the arm, and opening a fixing device on an end piece of the arm in order to drop a hose wound up on the end piece when the arm reaches the extended position.

Opening the fixing device can involve removing a securing element by means of a holding element which is flexible and resistant to tension and is connected to the container. Here, the holding element has a free length outside the container which is less than or corresponds to the free length of the extended arm outside the container, with the result that, on reaching the length of the holding element, the securing element is pulled out of the fixing device when the arm reaches the extended position. This can likewise affect a plurality of different holding elements of different lengths which are used to release additional oxygen masks at other end positions assigned to other seats.

Finally, the invention also relates to an aircraft, having a cabin with a plurality of seats and at least one partition between two of the seats, as well as a recess, arranged thereabove, in which at least one above-explained device for the provision of oxygen masks when required is arranged. The recess can involve a supply duct or a cutout in a ceiling panel.

BRIEF DESCRIPTION OF THE DRAWINGS

Further features, advantages and possible uses of the present invention will be found in the following description of the embodiment examples and the figures. Here, all the features described and/or depicted, in themselves and in any desired combination, form the subject matter of the invention, even when considered independently of their combination in the individual claims or the dependency references thereof. In the figures, identical reference signs furthermore represent identical or similar objects.

FIGS. 1a, 1b, 1c, and 1d show a schematic side view of the device.

DETAILED DESCRIPTION

Figure 2:
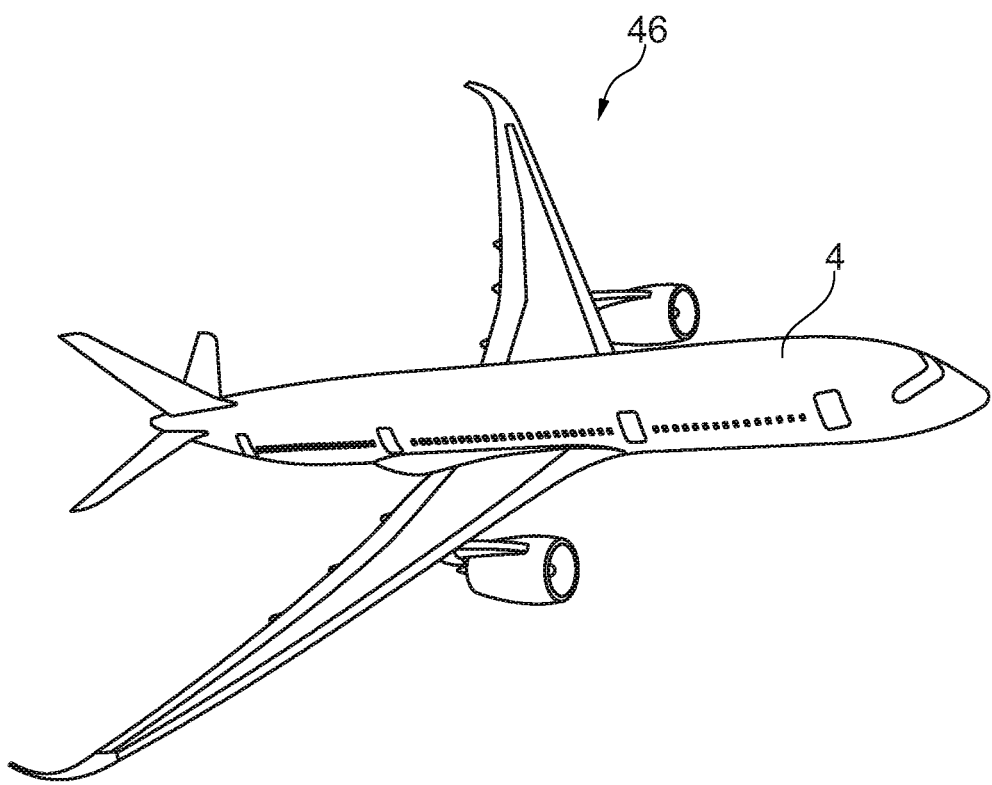
FIG. 2 shows a passenger aircraft having a cabin and passenger seats arranged therein as well as at least one device according to the invention.

FIGS. 1a, 1b, 1c, and 1d show an example of a device 2 according to an embodiment of the invention. Part of a cabin 4, in which there are several passengers 6 on adjacent passenger seats separated by partitions 8, is illustrated schematically. Above the passengers 6 there is a container 10, in which, purely by way of example, an oxygen cylinder 12 is positioned. This is in fluid communication with a plurality of oxygen masks 14 via a hose 20. However, it is also possible to use a central oxygen system, in which there are no separate oxygen cylinders 12 arranged in the containers 10.

To position the oxygen masks 14, arms 16 are provided, and these can be stowed in the container 10. In the illustration shown, a cover 18 of the container 10 is open, the cover being pivotable about an axis which, by way of example, is parallel to the transverse axis y of the cabin 4. A driving device 19, which moves the arms 16 from a retracted position into the extended position shown, is provided on the cover 18. The arms 16 are positioned directly above the outer passengers 6.

A two-stage movement of the oxygen masks 14 is provided to cross the partitions 8. This is illustrated by way of example in FIGS. 1b and 1c, in particular.

FIG. 1b shows an extended arm 16, on the end of which an end piece 22 having a fixing device 24 is arranged, on which the relevant oxygen mask 14 is secured. By way of example, the fixing device 24 has a magnetic sleeve 26 and a securing pin 28 which can be connected thereto as a securing element. The securing pin 28 projects through a through hole 30 in the end piece 22 of the arm 16 and fits into the magnetic sleeve 26. At one end 34, the securing pin 28 can hold a loop 32, which carries the wound-up hose 20.

The securing pin 28 is coupled to the container 10 or the cover 18 by means of a holding element in the form of a cord 36. The length of the cord 36 is somewhat less than the length of the arm 16 in the respective extended position, so that, when the end position of the arm 16 is reached, the securing pin 28 is pulled out of the sleeve 26 by means of the cord 36. The loop 32 can be secured on the end piece 22 by a first end 32a. After the securing pin 28 has been pulled out, a second end 32b of the loop 32 is loose and can no longer hold the wound-up hose 20. Thus, when the arm 16 is completely extended, the cord 36 ensures that the loop 32 is opened and the hose 20 released. As an alternative, the loop 32 can also be fixed on the hose 20 at a fastening point 33 and fastening on the end piece 22 is not required.

In order to prevent the magnetic sleeve 26 from falling out, it can be attached to the end piece 22 by means of a thread 38. Equally, the securing pin 28 and the cord 36 can be secured on the arm 16 and protected from falling out by means of another thread 40.

To accommodate the cord 36 in the container 10, a rotatably mounted drum 42 can be provided. By way of example, this has an axis of rotation 44 which extends perpendicularly to the direction of movement of the relevant arm 16. In the example, the axis of rotation 44 is arranged parallel to the longitudinal axis x of the vehicle cabin 4.

As soon as an oxygen mask 14 has been separated from the arm 16, it cannot be held at a defined height, for example. The oxygen mask 14 can fall in the direction of the passengers 6 or of the floor until it is held up by an obstacle. This can be a seat surface, an armrest, a shelf or the upper leg of a passenger. As a result, no additional components are necessary in order to stop the movement of the oxygen masks 14 again. The oxygen mask 14 is visible and reachable for passengers 6 both in a sitting and a recumbent position (see FIG. 1a). Consequently, there is no need for any "pull flags", i.e. pulling devices for pulling down the oxygen masks 14. The hoses 20 are accommodated in the respective oxygen masks 14 during packing to ensure that they take up as little space as possible in the container 10 in the storage position.

Consequently, reliable positioning of oxygen masks 14 can be achieved, even when there are obstacles to be overcome.

FIG. 2 shows an aircraft 46 which is equipped with a cabin 4 in which a plurality of passenger seats and at least one device 2 according to the above description are arranged.

For the sake of completeness, it should be noted that "having" does not exclude any other elements or steps and "a" or "an" does not exclude a multiplicity. It should furthermore be noted that features which have been described with reference to one of the above embodiment examples can also be used in combination with other features of other embodiment examples described above. Reference signs in the claims should not be regarded as restrictive.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A device for provision of one or more oxygen masks when required, comprising:
    a container configured to be closed by a cover, for accommodating the one or more oxygen masks;
    at least one extendable arm having an outer end; and
    at least one driving device,
    wherein the outer end is coupled to at least one of the one or more oxygen masks,
    wherein the at least one extendable arm is configured to adopt a storage position, in which the at least one extendable arm is arranged completely within the container, and at least one extended position, in which the outer end is extended out of the container and in which the at least one extendable arm holds the at least one of the one or more oxygen masks coupled thereto laterally at a distance from the container,
    wherein the at least one driving device is coupled to the at least one extendable arm for extension,
    wherein the at least one extendable arm has an end piece and a wound-up hose configured to be releasably fixed on the end piece, and
    wherein at least one fixing device is formed on the end piece in such a way as to release the wound-up hose when the at least one extended position is reached.

2. The device according to claim 1,
    wherein the at least one fixing device has a loop configured to be closed by a securing element to retain the hose,
    wherein the securing element is connected to the container by a holding element, the holding element being flexible and resistant to tension, and
    wherein the holding element has a free length outside the container less than or corresponding to a free length of the at least one extendable arm extended outside the container, with the result that, on reaching the free length of the holding element, the securing element is pulled out of the at least one fixing device when the at least one extendable arm reaches the at least one extended position.

3. The device according to claim 2, wherein the holding element is configured be held on a drum rotatably mounted in the container in such a way that the holding element is configured to be unwound.

4. The device according to claim 2, wherein the holding element is arranged in a guide channel of the container.

5. The device according to claim 2, wherein the at least one fixing device is configured to retain the securing element positively or non-positively in a releasable manner.

6. The device according to claim 2,
    wherein the at least one fixing device has a sleeve having a sleeve bore, and
    wherein the securing element has a securing pin corresponding to the sleeve bore.

7. The device according to claim 6, wherein the sleeve is magnetic, at least in some region or regions, and is configured to retain the securing pin magnetically in a releasable manner.

8. The device according to claim 1, wherein the at least one extendable arm comprises at least two extendable arms having different lengths in their respective extended positions thereof.

9. The device according to claim 1, wherein the at least one extendable arm comprises at least two extendable arms configured to be extended in different directions.

10. An aircraft having a cabin with a plurality of seats and at least one partition between two of the plurality of seats, and having a recess arranged above the plurality of seats and the at least one partition, comprising at least one device for the provision of the one or more oxygen masks according to claim 1.

11. A method for a selective provision of at least one oxygen mask in an aircraft, comprising:
 opening a cover of a container arranged in a recess in a ceiling region;
 extending an arm from a storage position into an extended position by a driving device, wherein at least one oxygen mask is coupled to the arm; and
 opening at least one fixing device on an end piece of the arm to drop a hose wound up on the end piece when the arm reaches the extended position.

12. The method according to claim 11, wherein opening the at least one fixing device includes removal of a securing element by a holding element, wherein the holding element is flexible and resistant to tension and is connected to the container, and outside the container, has a free length less than or corresponding to a free length of the extended arm outside the container.

* * * * *